(12) United States Patent
Sowers et al.

(10) Patent No.: US 8,945,906 B2
(45) Date of Patent: Feb. 3, 2015

(54) ORGANIC BIOFILM SUBSTRATA AS A MICROBIAL INOCULUM DELIVERY VEHICLE FOR BIOAUGMENTATION OF PERSISTENT ORGANIC POLLUTANTS IN CONTAMINATED SEDIMENTS AND SOILS

(75) Inventors: Kevin R. Sowers, Baltimore, MD (US); Birthe Kjellerup, Ellicott City, MD (US); Upal Ghosh, Ellicott City, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 150 days.

(21) Appl. No.: 13/177,436

(22) Filed: Jul. 6, 2011

(65) Prior Publication Data

US 2012/0021493 A1 Jan. 26, 2012

Related U.S. Application Data

(60) Provisional application No. 61/361,818, filed on Jul. 6, 2010.

(51) Int. Cl.
| | | |
|---|---|---|
| *C12N 1/12* | (2006.01) | |
| *C12N 1/20* | (2006.01) | |
| *A62D 3/02* | (2007.01) | |
| *B09C 1/10* | (2006.01) | |
| *A62D 101/22* | (2007.01) | |

(52) U.S. Cl.
CPC .. *C12N 1/20* (2013.01); *A62D 3/02* (2013.01); *B09C 1/10* (2013.01); *A62D 2101/22* (2013.01)
USPC .......................... 435/252.1; 435/248; 435/262

(58) Field of Classification Search
None
See application file for complete search history.

(56) References Cited

U.S. PATENT DOCUMENTS

| 7,001,519 B2 | 2/2006 | Linden et al. |
|---|---|---|
| 7,824,129 B2 | 11/2010 | Ghosh et al. |
| 2011/0015064 A1 | 1/2011 | Ghosh et al. |

OTHER PUBLICATIONS

Bouwer et al., Environ. Sci. Technol., 1982, vol. 16, p. 836-843.*
Wu et al., Appl. Environ. Microbiol. 2002, vol. 68, No. 2, p. 807-812.*
Cho et al., Marine Environmental Research, 2007, vol. 64, p. 541-555.*
Leigh et al., Applied and Environmental Microbiology, 2006, vol. 72, No. 4, p. 2331-2342.*
Lündsdorf et al., Environmental Microbiology, 2000, vol. 2, No. 2, p. 161-168.*
Abraham, W., et al., "Polychlorinated biphenyl-degrading microbial communities in soils and sediments", "Current Opinion in Microbiology", May 13, 2002, pp. 246-253, vol. 5.

Aulenta, F., et al., "Anaerobic bioremediation of groundwater containing a mixture of 1,1,2,2-tetrachloroethane and chloroethenes", "Biodegradation", 2006, pp. 193-206, vol. 17.
Berkaw, M., et al., "Anaerobic ortho Dechlorination of Polychlorinated Biphenyls by Estuarine Sediments from Baltimore Harbor", "Applied and Environmental Microbiology", Jul. 1996, pp. 2534-2539, vol. 62, No. 7.
Cornelissen, G., et al., "Extensive Sorption of Organic Compounds to Black Carbon, Coal, and Kerogen in Sediments and Soils: Mechanisms and Consequences for Distribution, Bioaccumulation, and Biodegradation", "Environmental Science & Technology", Aug. 5, 2005, pp. 6881-6895, vol. 39, No. 18.
Fagervold, S., et al., "Sequential Reductive Dechlorination of meta-Chlorinated Polychlorinated Biphenyl Congeners in Sediment Microcosms by Two Different Chloroflexi Phylotypes", "Applied and Environmental Microbiology", Dec. 2005, pp. 8085-8090, vol. 71, No. 12.
Fagervold, S., et al., "Microbial Reductive Dechlorination of Aroclor 1260 in Baltimore Harbor Sediment Microcosms Is Catalyzed by Three Phylotypes within the Phylum Chloroflexi", "Applied and Environmental Microbiology", May 2007, pp. 3009-3018, vol. 73, No. 9.
Kjellerup, B., et al., "Site-specific microbial communities in three PCB-impacted sediments are associated with different in situ dechlorinating activities", "Environmental Microbiology", 2008, pp. 1296-1309, vol. 10, No. 5.
Krumins, V., et al., "PCB dechlorination enhancement in Anacostia River sediment microcosms", "Water Research", Aug. 9, 2009, pp. 4549-4558, vol. 43.
Kobe, M., et al., "Genome sequence of the chlorinated compound-respiring bacterium *Dehalococcoides* species strain CBDB1", "Nature Biotechnology", Aug. 21, 2005, pp. 1269-1273, vol. 23, No. 10.
May, H., et al., "Dehalorespiration with Polychlorinated Biphenyls by an Anaerobic Ultramicrobacterium", "Applied and Environmental Microbiology", Apr. 2008, pp. 2089-2094, vol. 74, No. 7.
Mullin, M., et al., "High-Resolution PCB Analysis: Synthesis and Chromatographic Properties of All 209 PCB Congeners", "Environ. Sci. Technol", 1984, pp. 468-476, vol. 18.
Rhodes, A., et al., "Impact of activated charcoal on the mineralisation of 14C-phenanthrene in soils", "Chemosphere", Feb. 19, 2010, pp. 463-469, vol. 79.

(Continued)

*Primary Examiner* — Kade Ariani
(74) *Attorney, Agent, or Firm* — Hultguist, PLLC; Mary B. Grant

(57) ABSTRACT

A system and methods for removal of persistent organic pollutants (POPs) from an environment, where the system includes an inert and organic biofilm substrata as biofilm media for dual use: 1) inoculation of microorganisms to degrade POPs and 2) accumulation of POPs on the substrata, effective in maintaining bioavailable concentrations for sustaining microbial activity. Microorganisms capable of degrading or transforming POPs are actively associated with the substrata as a biofilm. Application of this delivery vehicle will enhance the microbial degradation of POPs, while simultaneously adsorbing hydrophobic POPs from the environment making them bioavailable for the microorganisms located in the formed biofilms and additionally lowering the aqueous concentration of POPs that have detrimental effects towards fish and mammals as they bioaccumulate through the food chain.

14 Claims, 12 Drawing Sheets

(56) References Cited

OTHER PUBLICATIONS

Robles-Gonzalez, I., et al., "A review on slurry bioreactors for bioremediation of soils and sediments", "Microbial Cell Factories", Feb. 29, 2008, pp. 1-16, vol. 7, No. 5.

Seshadri, R., et al., "Genome Sequence of the PCE-Dechlorinating Bacterium *Dehalococcoides* ethenogenes", "Science", Jan. 7, 2005, pp. 105-108, vol. 307.

Sun, X., et al., "The Effect of Activated Carbon on Partitioning, Desorption, and Biouptake of Native Polychlorinated Biphenyls in Four Freshwater Sediments", "Environmental Toxicology and Chemistry", Jun. 2, 2008, pp. 2287-2295, vol. 27, No. 11.

Wu, Q., et al., "Dechlorination of Chlorobenzenes by a Culture Containing Bacterium DF-1, a PCB Dechlorinating Microorganism", "Environ. Sci. and Technol.", 2002, pp. 3290-3294, vol. 36.

NOTE: For the non-patent literature citations that no month of publication is indicated, the year of publication is more that 1 year prior to the effective filing date of the present application.

\* cited by examiner

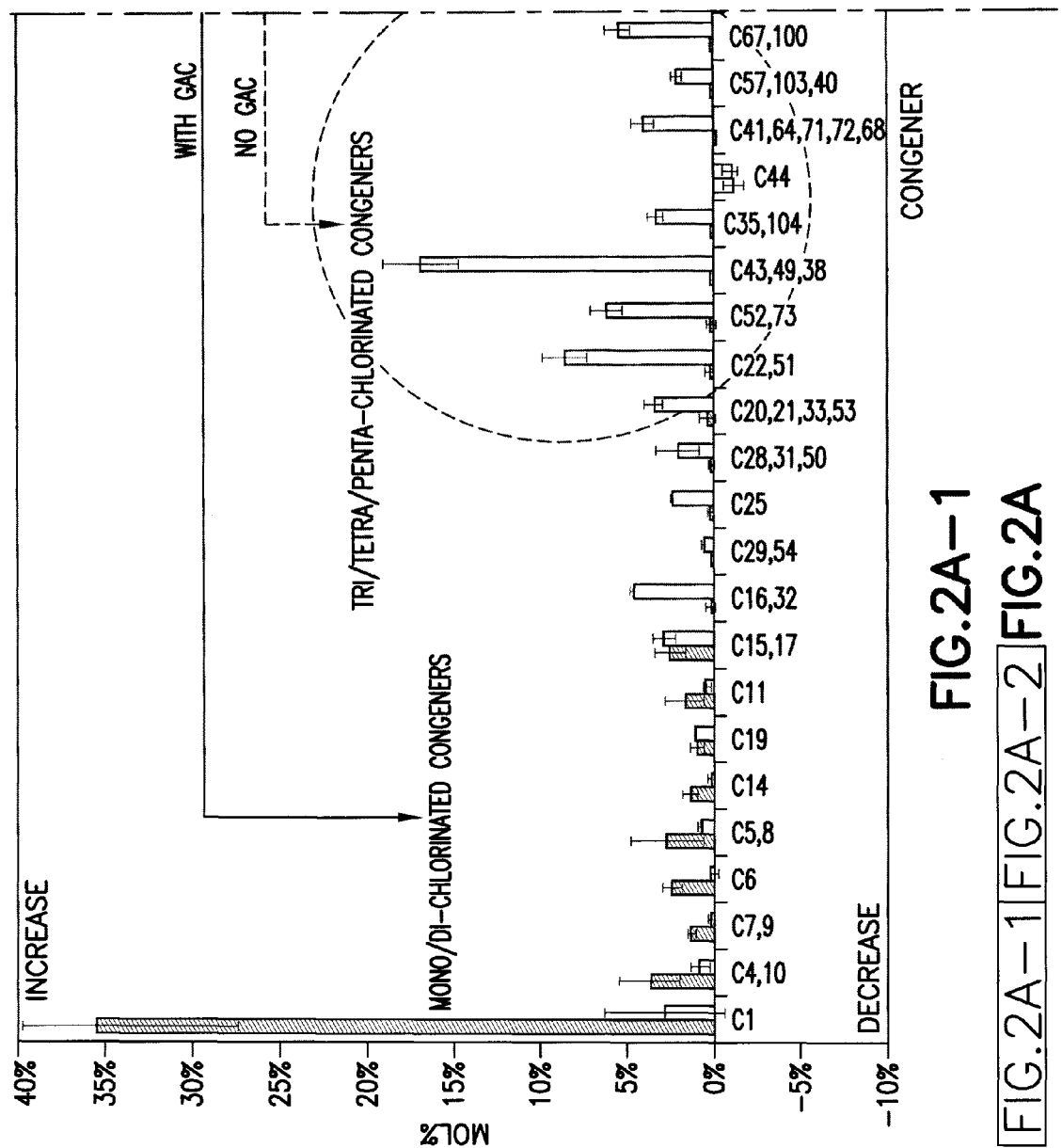

ORGANIC BIOFILM SUBSTRATA AS A MICROBIAL INOCULUM DELIVERY VEHICLE FOR BIOAUGMENTATION OF PERSISTENT ORGANIC POLLUTANTS IN CONTAMINATED SEDIMENTS AND SOILS

CROSS REFERENCE TO RELATED APPLICATIONS

This application claims the benefit of U.S. Provisional Application No. 61/361,818, filed Jul. 6, 2010. The disclosure such application is hereby incorporated herein by reference in its entirety, for all purposes.

GOVERNMENT RIGHTS IN THE INVENTION

This invention was made with government support under a grant awarded by the United States Department of Defense's Strategic Environmental Research and Development Program Grant No. ER1502. The invention was further made with government support under a grant awarded by the Department of Defense Office of Naval Research Grant No. N000140310035. The government has certain rights in the invention.

FIELD OF THE INVENTION

The present invention relates to a persistent organic pollutant (POP)-degrading system containing a substratum and a biofilm containing POP-degrading bacteria and where the system is capable of adsorbing and degrading the POPs. The invention further relates to methods of treating POP-contaminated sediment or soil and methods of inoculating microorganisms for POPs, using such a system. Still further, the invention relates to a method of making such a system.

DESCRIPTION OF THE RELATED ART

Persistent organic pollutants (POPs) are pollutants present in the environment, globally dispersed throughout the ecosystem as a result of cycling between air, water, and soil. Polychlorinated biphenyls (PCBs) are persistent organic pollutants that are hydrophobic and, as a result of their hydrophobicity, PCBs bioaccumulate throughout the food chain by absorption in the fatty tissue of animals and humans where they have been reported to act as endocrine disrupters and possible carcinogens.

Bioaugmentation is the introduction of natural microorganisms (or a variant thereof) a genetically engineered variant (inoculums) to treat contaminated soil or water. At sites where soil and groundwater are contaminated with POPs, bioaugmentation is used to ensure that the in situ microorganisms can completely degrade these contaminants to non-toxic elements.

Bioaugmentation has been practiced for decades in agriculture and wastewater treatment and more recently for bioremediation of POPs in contaminated aquifers, waste streams or confined areas such as landfills (Aulenta, F., et al., (2006), *Biodegradation* 17(3):193-206; Robles-Gonzalez IV, et al., (2008), *Microb. Cell Fact.* 7:5). However, common for these approaches has been the demand for either a confined system such as a slurry reactor or a liquid system such as groundwater. In these situations bioaugmentation has been based on liquid bacterial cultures as inoculum.

Degradation of less volatile POPs (e.g., PCBs, chlorobenzenes, etc.) occurring under anaerobic conditions in sediments and soil is a critical process for their complete transformation to non-toxic forms. When grown in liquid culture, the density of many aromatic POP-transforming microorganisms such as the PCB dechlorinating bacteria is low, leading to low efficiency of the progression of the reaction between the microorganisms and the POPs. Specifically, in liquid culture, the POPs are not highly bioavailable to the microorganisms.

In sediment and soil, in situ microbial degradation of POPs under anaerobic conditions is a slow process due to the chemical and biological stability of the contaminants, the low bioavailable concentrations of individual contaminants and, in many cases, the low abundance, diversity, and activity of naturally occurring POP degrading microorganisms. Therefore, it has been suggested that in situ biological transformation of POPs in sediment and soil will not reduce the concentration sufficiently within a reasonable time frame. Based on the conclusion that the affected sediment and soil sites are untreatable, the removal of POPs in situ has been achieved by removal of the affected sediment and soil sites by dredging of the sites, and removal of the dredge spoil to contained locations such as landfills.

However, the action of removal of impacted sediments and soil can cause unwanted release of POPs into the environment. The physical disturbance due to dredging will impact benthic organisms in the environment directly and the concentration of POPs in the water phase will increase due to re-suspension of sediment particles containing POPs. This will cause harm for benthic organisms and the surrounding environment since the contaminated sediment will be spread. Activated carbon has been used for sequestration of less volatile POPs such as PCBs and PAHs to prevent these contaminants from entering the water column in cases of dredging or at heavily contaminated sites, where the solid-liquid equilibrium results in the presence of POPs in the water phase. The results from both laboratory and field studies show that activated carbon is very effective in removing POPs from the water phase and thereby reducing the toxicity towards benthic organisms (Sun X, Ghosh U. (2008), *Environ. Toxicol. Chem.*, 27, 2287-2295.). In addition, since the activated carbon is mixed with the sediment (e.g., by injection or tilling), the particles cannot be distinguished from sooth, black carbon and other organic particles that are naturally present in the sediment.

There therefore remains a need in the art for a system of POP reduction or removal effective in bioaugmentation of POP-contaminated sediments and soils, where the inoculum is not supplied as a liquid culture and where the system is useful both in confined systems and in situ.

SUMMARY OF THE INVENTION

The present invention relates to a system and method useful in reduction or removal of POPs from POP-contaminated sediment or soil, treatment of contaminated sediment or soil and inoculation of microorganisms for POPs.

In one aspect the invention provides a system for at least partially reducing persistent organic pollutants (POPs) from an environment, the system comprising: an inert substratum effective to adsorb hydrophobic POPs; and a biofilm on the substratum, wherein the biofilm comprises an active inoculum.

In another aspect the invention provides a method of making a system for at least partially reducing POPs from an environment, the method comprising formation of a biofilm on a substratum effective to adsorb hydrophobic POPs, wherein the biofilm comprises an active inoculum.

In a still further aspect the invention provides a method of treating a POP-containing environment, the method comprising administration of a system to the POP-containing environment, the system comprising: an inert substratum effective to adsorb hydrophobic POPs; and a biofilm on the substratum, wherein the biofilm comprises an active inoculum and wherein the system is effective to at least partially reduce POPs in the POP-containing environment.

In yet another aspect the invention provides a method of reducing POPs in a locus containing the same, comprising introducing to said locus a biofilm comprising an active inoculum supported on a hydrophobic surface.

In another aspect the invention provides a method of bioaugmenting an aerobic dechlorination system, the method comprising administration of an anaerobic dechlorination system comprising: an inert substratum effective to adsorb hydrophobic POPs and a biofilm on the substratum, wherein the biofilm comprises an active inoculum.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
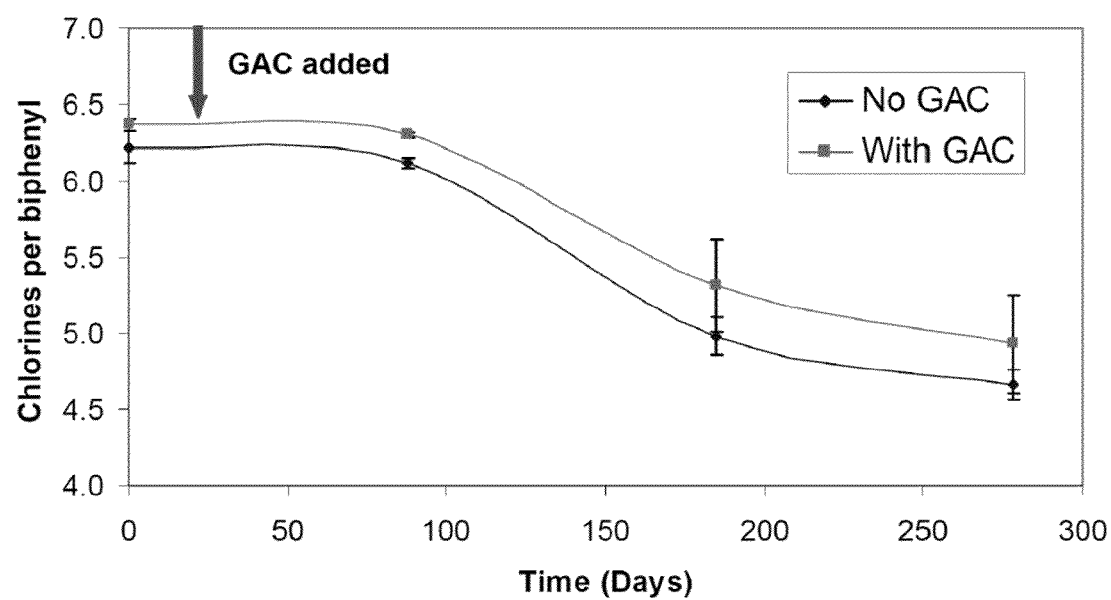
FIG. 1 is a graph demonstrating the reductive dehalogenation of Aroclor 1260 in Baltimore Sediments microcosms incubated with and without GAC, as detailed in Example 1 below.

The present invention relates to a system useful in reduction or removal of POPs from a POP-contaminated environment via bioaugmentation and methods of making such a system. The invention further relates to methods of treating a POP-contaminated environment employing such a system. The invention further relates to methods of inoculating microorganisms for POPs, employing such a system.

A POP-containing or POP-contaminated environment, as used herein is any environment in which POPs are found to have accumulated. Environments in which a system of the invention are useful include, but are not limited to soil or sediment present in agricultural or aquacultural systems, wastewater systems, water treatment systems or natural or man-made bodies of water such as harbors, bays, lakes, rivers, oceans and the like. In various embodiments, a system of the invention is useful in situ, in such environments, or is useful in the treatment of soil or sediment retrieved from such environments.

"Persistent organic pollutants" or "POPs" as used herein, refer to organic compounds resistant to normal, environmental degradation. POPs often have low or medium volatility and low water solubility. Due to these qualities, POPs are known to accumulate in various environments, both in natural, in situ environments, and in confined, closed or controlled environments, e.g., an aquaculture system. The less-volatile hydrophobic POPs often adsorb to sediment and/or soil particles of such environments. Examples of POPs include: polyaromatic hydrocarbons (PAHs), polyhalogenated aromatic hydrocarbons, polycyclic aromatic hydrocarbons, polychlorinated biphenyls, chlorinated aromatics, organochlorine pesticides, dioxins, benzofurans, polychlorinated biphenyls (PCBs), chlorobenzenes, chlorophenols, carbon tetrachloride, aldrin, chlordane, dichlorodiphenyl trichloroethane (DDT), dieldrin, endrin, heptachlor, hexachlorobenzene, mirex, toxaphene, polychlorinated dibenzo-p-dioxins (dioxins), polychlorinated dibenzofurans (furans) and the like.

PCBs, as one type of POP, raise concerns due to their stability, toxicity and ability to bioaccumulate, as with other POPs. There are 209 PCB congeners that have been identified and numbered. While particular examples of PCBs as POPs are provided herein, the system and methods of the invention relate generally to reduction or removal of any POP with a low aqueous solubility and with a microorganism capable of selectively attacking that POP.

Microorganisms useful in the system and methods of the invention are microorganisms that can attack, degrade, reduce, transform or otherwise affect the POPs, including rendering them more subject to degradation by native microorganisms.

By the present invention it was determined that the efficiency seen in liquid culture methods of administration of POP-degrading microorganisms could be improved by providing a hydrophobic surface to which the POPs can adsorb. Such adsorption to hydrophobic surfaces increases the bioavailable concentration of the POPs to the microorganisms. Therefore, the present invention provides a system for bioaugmentation, to enhance the naturally occurring transformation of POPs in the environment using efficient delivery vehicles for supply of a highly active inoculum.

An "active inoculum," as used herein, refers to a microorganism added to a POP-contaminated environment which affects the POPs in a manner that degrades them and/or makes them more subject to degradation. In one embodiment, the active inoculum is a POP-degrading bacteria or a POP-transforming bacteria.

Microorganisms useful as an active inoculum in the system and methods of the invention may include, but are not limited to, dehalorespiring microorganisms, such as, *Dehalococcoides* spp., *Dehalobium* spp., *Desulfitobacterium* spp., *Desulfomonile* spp., *Geobacter* spp. and PCB oxidizing bacteria, such as, *Burkholderia* spp., *Rhodococcus* spp., *Luteibacter* spp., and *Williamsia* spp.

The substrata of the invention are solids, which may be constructed from a variety of organic materials into a variety of shapes and sizes. For example, activated carbon can be used, in a granular, powdered or otherwise useful form. The substratum is comprised of an inert substance and does not limit the activity of the active inoculum. In a particular embodiment, the substratum provides a stimulatory effect to the activity of the active inoculum. In a particular embodiment, the substrata comprise granulated activated carbon (GAC). In a further embodiment, the substratum comprises any known or commercially available organic substratum.

The substrata contain a biofilm comprised of an active inoculum formed thereon. Microorganisms capable of degrading POPs will be actively associated with the substrata as a biofilm. In one embodiment of the invention, the POP-degrading bacteria are surrounded by hydrophobic layers that enable the individual bacterial cells to align in close proximity to particles and thereby interact with hydrophobic POPs that often are adsorbed to surfaces in the aquatic environment due to their hydrophobic nature. By supplying a hydrophobic surface as a growth medium, the POP-degrading bacteria forms a biofilm on the substratum, where the biofilm has a much larger cell density than would be possible to obtain in liquid cultures and therefore is very effective as inoculum for bioaugmentation in the environment.

The system of the invention therefore provides an inert and organic biofilm substratum as a biofilm media for dual use, including both: 1) inoculation of microorganisms to degrade persistent organic pollutants (POPs) and 2) accumulation of these POPs to maintain bioavailable concentrations for sustaining microbial activity.

In one embodiment, the invention provides a system for reduction or removal of POPs from POP-contaminated environment (e.g., aqueous environment containing sediment and/or soil), where the system comprises an inert substratum and a biofilm comprising an active inoculum formed thereon, and the system is capable of adsorbing and degrading hydrophobic POPs from the environment in which the system is applied. In a particular embodiment, the POPs are PCBs.

It was previously believed that an active inoculum would not function to degrade POPs in the presence of carbon due to reduced bioavailability to the microorganism. Contrary to that commonly held assumption, the present invention demonstrates that use of carbon as a substrate for the active inoculum and the POPs both permits and stimulates the degradation of POPs. The presence of the solid substrata in the system of the invention allows for administration of the system and the incorporated biofilm to the environment to be treated in a solid form, as an alternative to supplying POP-degrading organisms as liquid cultures for bioaugmentation. The system of the present invention provides faster and more selective degradation of POPs, as compared to previous systems and methods.

Figure 4:
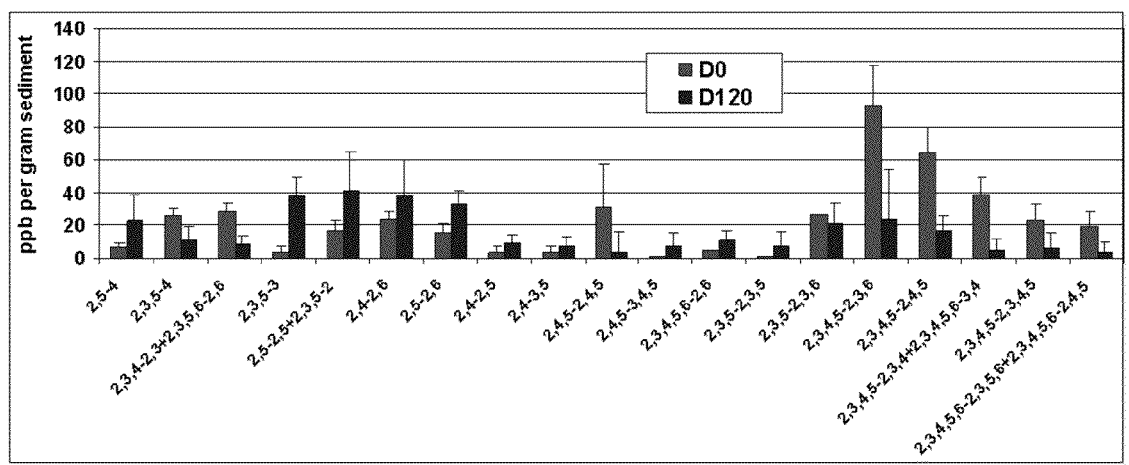
FIG. 4 is a graph demonstrating the successful dechlorination of PCB-contaminated sediment collected from Baltimore Harbor, Md. in the presence of *Dehalobium chlorocoercia*, DF-1, illustrating the effects on dominant PCB congeners.
Figure 5:
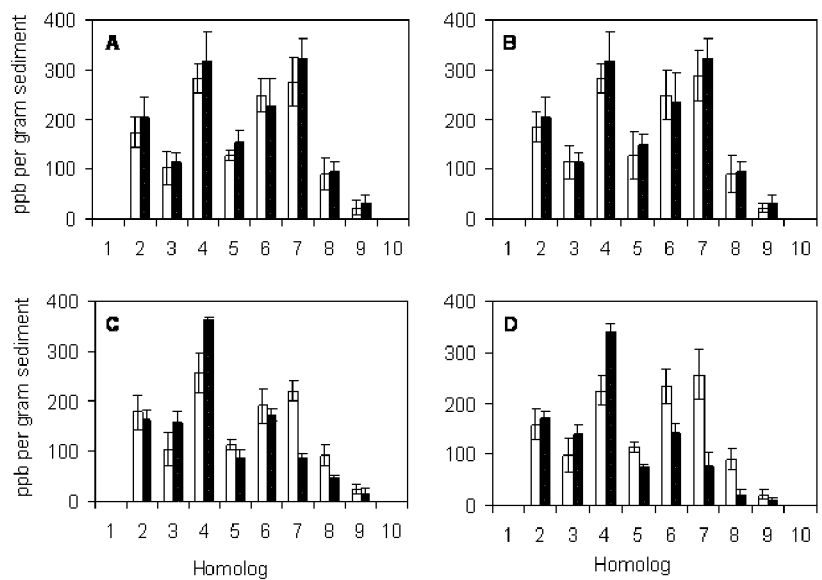
FIG. 5 is a graph demonstrating PCB analysis by homolog at day 0 (white bars) and day 120 (black bars) after treatment as described in Example 2, with (A) filter sterilized spent growth medium, (B) sterilized spent growth medium and GAC, (C) concentrated DF1 in growth medium inoculated directly into the sediment, and (D) concentrated DF1 adsorbed onto GAC.
Figure 6:
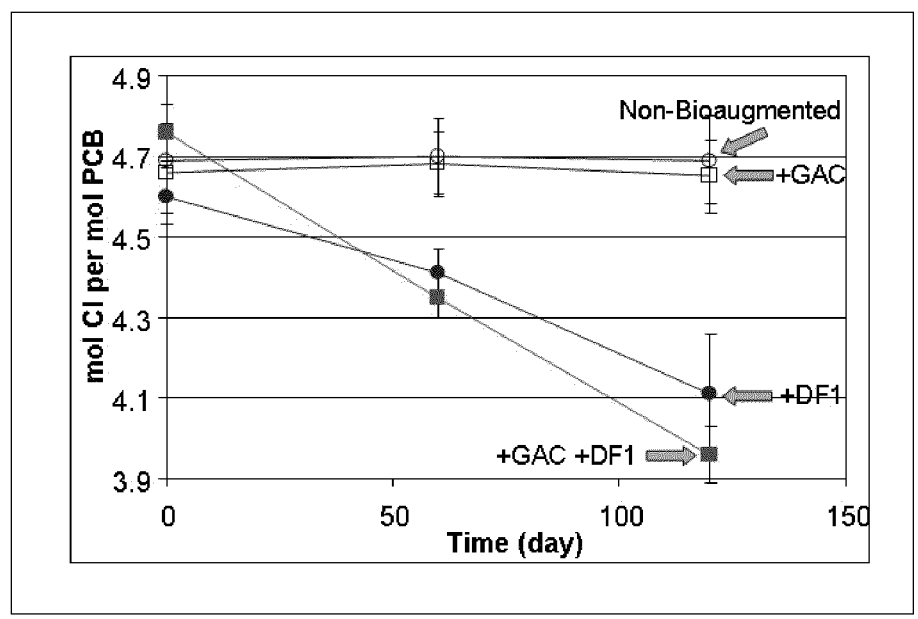
FIG. 6 is a graph demonstrating the changes in mols Cl per mols PCB in mesocosms containing sediment contaminated with low levels of Aroclor 1260 over time after treatment with an anaerobic PCB dechlorinator.

In one embodiment, cultured PCB dehalorespiring bacteria may be used as an active inoculum in a system of the invention, as exemplified in Example 2 herein. As seen in FIGS. 4-6, the dehalorespiring *Dehalobium chlorocoercia* DF1 stimulated dechlorination of PCBs and resulted in a significant decrease of PCBs in the environment. Results presented in FIG. 4 show that addition of DF-1 to PCB contaminated sediment using GAC for inoculating the dehalorespiring bacteria accelerated the reductive dechlorination of weathered PCB congeners even after 120 days of incubation. The sustabinability of such system is shown in Example 3 below.

In a further embodiment, a system of the invention provides reductive dechlorination of higher chlorinated congeners to lower chlorinated congeners. As demonstrated herein, bioaugmentation with the dehalorespiring bacterium DF-1 successfully stimulated the reductive dechlorination of sediment containing 1.3 ppm of weathered Aroclor 1260. Similarly highly chlorinated congeners that may be reductively dechlorinated by a system of the invention include, but are not limited to Aroclor 1016, 1221, 1232, 1242, 1248, 1254, 1258, 1260, 1262, 1268, and various commercial PCB mixtures, known under trade names such as Aroclor, Inerteen, Pyranol, Abestol, Askarel, Bakola131, Chlorextol, Hydol®, Noflamol, Saf-T-Kuhl, and Therminol® in the United States, Kanechlor, Santotherm, and Pyrochlor in Japan, Askarel in the United Kingdom, Phenoclor, and Pyralene in France, Clophen in Germany, and Fenclor in Italy.

A system of the invention, comprising substrata and a biofilm comprising an active inoculum, is effective in bioaugmentation of a PCB or other POP-contaminated environment. A system of the invention must be sustainable within the indigenous microbial community, must not interfere with the bioavailability of the levels of PCB or other POPs targeted in the environment and must effectively disperse into the environment to be treated.

Bioavailability

Figures 2, 2A:
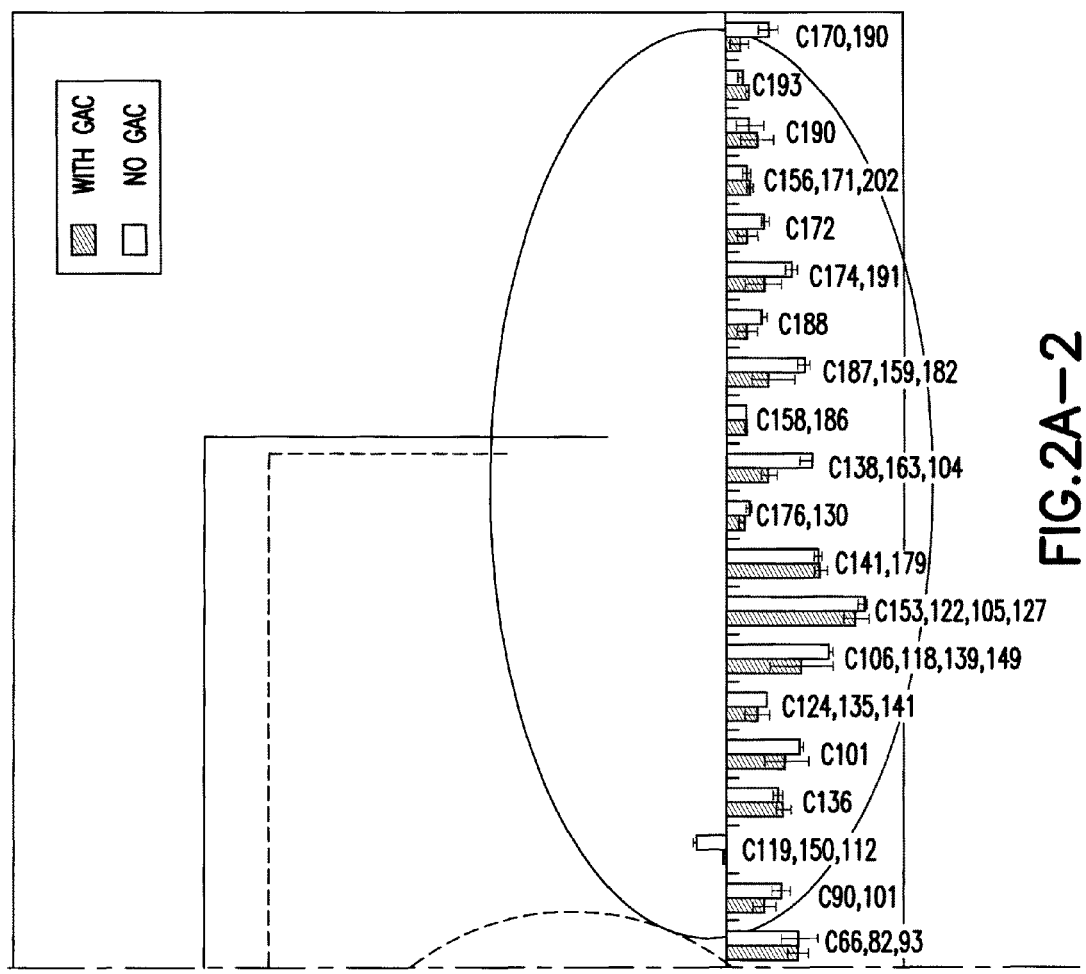
FIGS. 2A and 2B are graphs demonstrating the PCB dechlorination activity of sediment collected from Baltimore Harbor, Md. in the presence/absence of activated carbon showing effects of GAC on dechlorination products from Aroclor 1260 as individual congeners (A) and congeners homologs (B).
Figure 2B:
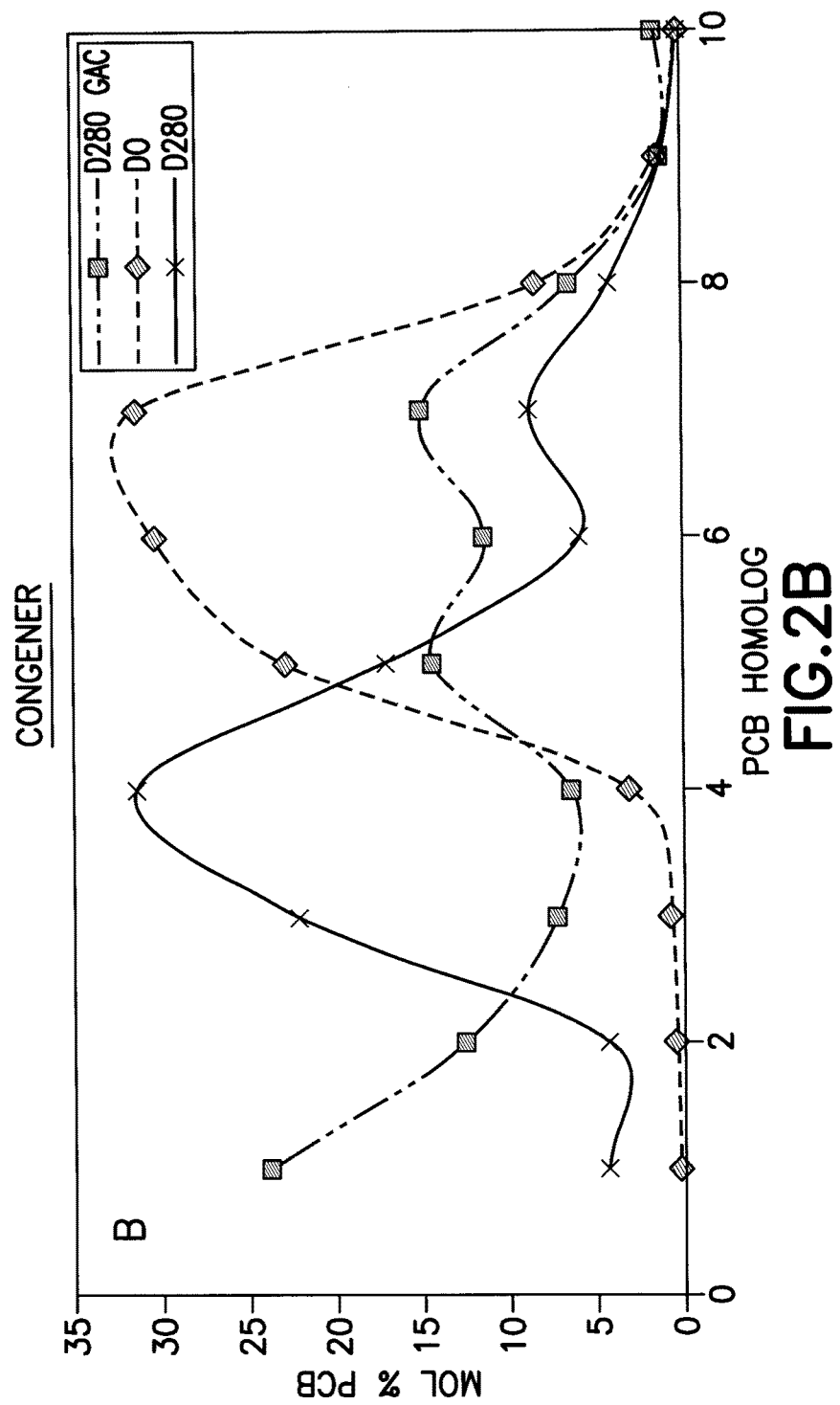

Example 2 demonstrates that bioaugmentation with the dehalorespiring bacterium DF-1 successfully stimulated the reductive dechlorination of sediment containing 1.3 ppm of weathered Aroclor 1260. Furthermore, addition of GAC, which increases the partition coefficient of the PCB between the sediment matrix and aqueous phase, had no inhibitory effect on dechlorination activity in bioaugmented mesocosms, as compared with no GAC treatment. As illustrated by FIG. 2A, the addition of GAC promoted a more extensive anaerobic microbial transformation of commercial complex PCB mixtures to less chlorinated congeners compared with sediment microcosms without GAC. This is contrary to earlier teachings that increasing the partition coefficient of PCBs with organic carbon, which effectively reduces the bioavailability of PCBs to macroorganisms, would also reduce the bioavaiability to micoroorganisms. It is further contemplated by the present invention that PCB dehalorespiring bacteria have mechanisms that enable them to compete for PCBs in environments containing high amounts of organic carbon.

In one embodiment, a system of the invention, comprising substrata and a biofilm comprising an active inoculum, is effective in stimulation of reductive dechlorination of low levels of weathered PCBs in the 1-2 ppm range even in the presence of a high background of organic carbon.

Sustainability

In one embodiment, a system of the invention includes an active incoulum that effectively competes with bacteria present within the environment to be treated, to effectively bioaugment the degradation system within the environment.

Figure 9:
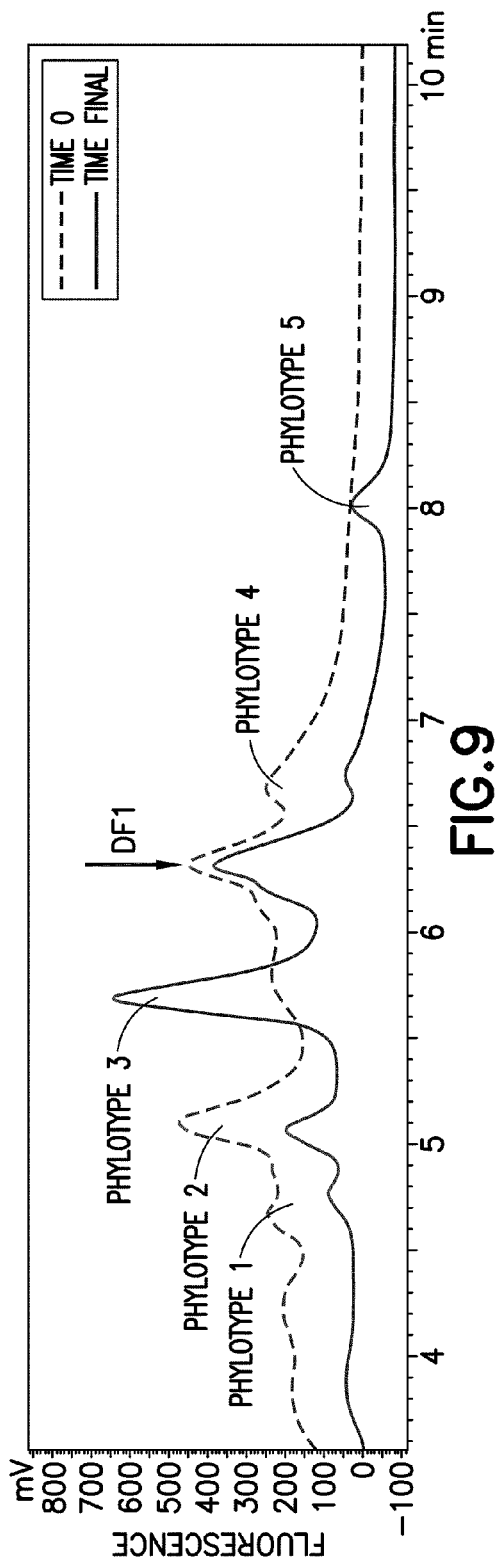
FIG. 9 is a graph illustrating DHPLC community analysis of dechlorinator phylotypes in a mesocosm with DF-1.

In an embodiment where the POP is a PCB, the active inoculum must compete with the indigenous community of non-dehalorespiring bacteria for electron donors and nutrients, and with the indigenous dehalorespiring community for low levels of PCBs in order to successfully bioaugment weathered PCB-impacted sediments. In Example 3, DF-1 was detected in bioaugmented sediment mesocosms after 120 days indicating that bioaugmentation was competitive with a low concentration of weathered Aroclor in a background of the indigenous sediment community. The total numbers of dehalorespiring bacteria decreased by approximately half after 60 days to a steady state of $7-8 \times 10^5$ cells per gram of sediment (FIG. 7), but community analysis showed that DF-1 was retained as a predominant member of the dehalorespiring population (FIG. 9). The total numbers of dehalorespiring phylotypes was 1-2 orders of magnitude lower than observed in prior reports of Aroclor 1260 dechlorinating microcosms, but unlike the prior studies an electron donor was not added and the lower steady state numbers appear to reflect lower concentrations of indigenous electron donor available in the sediment.

The sustainment of the dehalorespiring bacteria in the sediment mesocosms without an exogenous electron donor is consistent with the ability of dehalorespiring bacteria to outcompete hydrogenotrophic sulfate reducers, acetogens, and methanogens in the presence of limited hydrogen concentrations. Indigenous phylotypes of dehalorespiring bacteria, with the exception of phylotype DEH10 had not been reported previously in Baltimore Harbor sediment Aroclor 1260 enrichment microcosms. However, in addition to supporting this indigenous population of dehalorespiring bacteria, the results show that DF-1 was able to compete successfully with the indigenous microbial population even with the lower background of electron donor.

Further, the detection of PCB congeners not resulting from dechlorination of doubly flanked chlorines were observed. The detection of indigenous dehalorespiring phylotypes throughout the incubation period in the current study (FIG. 8) support the conclusion that DF-1 had a stimulatory effect on the indigenous dehalorespiring community. One possible explanation for this effect is "priming" by the accumulation of dechlorination products from the initial activity of high numbers of DF-1 inoculated into the sediments. Addition of PCB congeners and analogs is known to stimulate the reductive dechlorination of PCBs in lab studies and in field tests. Overall, the results demonstrate that, in addition to initiating and directly dechlorinating weathered PCBs, bioaugmentation with DF-1 had a synergistic effect on the indigenous dehalorespiring community.

Bioaugmentation

There have been numerous reports on the potential of aerobic bioaugmentation with bacteria, fungi and plants, but these processes have limited capacity to attack highly chlorinated congeners often found in PCB impacted sites (Abraham, W. R., et al., *Curr Opin Microbiol.*, 2002, 5, 246-253). Reductive dechlorination of higher chlorinated PCB congeners has the potential to complement these processes but there have been very few studies to date describing the use of anaerobic bioaugmentation to stimulate in situ treatment of PCB impacted sediments.

Previous attempts to stimulate the reductive dechlorination of weathered PCBs in sediment microcosms by bioaugmentation without adding a halogenated congener as a primer were unsuccessful. There have been recent attempts to test the effects of bioaugmentation with pure cultures of dehalorespiring bacteria. Krumins et al. (Krumins, V., *Water Res.*, 2009, 43, 4549-4558) reported enhanced reductive dechlorination of weathered PCBs (ca. 2 ppm) in Anacostia River sediment microcosms after bioaugmentation with *D. ethenogenes* strain 195 and May et al. (May, H. D., et al., *Appl Environ Microbiol.*, 2008, 74, 2089-2094) reported enhanced dechlorination of Aroclor impacted soil (4.6 ppm) after bioaugmentation with DF-1.

In contrast to the prior studies where bioaugmentation with pure cultures of dehalorespiring bacteria stimulated the reductive dechlorination of PCB by 0.2 Cl/biphenyl after 415 days and 0.35 Cl/biphenyl after 145 days, respectively, bioaugmentation in the current study stimulated the reductive dechlorination by 0.7 Cl/biphenyl after only 120 days. Furthermore, bioaugmentation results in the present invention stimulated 56% by mass reduction of penta- through nonachlorobiphenyls to mono- through tetrachlorobiphenyls, which are susceptible to aerobic degradation, with no detectable activity in untreated controls. The discrepancies in the rates and extent of dechlorination could possibly occur due to a number of factors including available nutrients, presence of inhibitory co-contaminants, the dehalorespiring strain used and the growth state and numbers of cells used for bioaugmentation. Distribution of cells in the present invention was effective either by direct injection or on GAC particles. The ability to use a solid substrate, such as GAC, for inoculation of cells provides a method for dispersing cells in the field.

In one embodiment, a system of the invention, comprising substrata and a biofilm comprising an active inoculum, is effective in anaerobic reductive dechlorination of higher chlorinated PCB congeners and demonstrate the ability to disperse within an environment to be treated.

In a further embodiment, the invention provides a method of bioaugmentation of an aerobic biotransformation method by combining the aerobic biotransformation method with a system of the invention. Anaerobic bioaugmentation of the aerobic biotransformation method is effective to achieve combined POP degradation. Such resultant degradation is more complete than either of the aerobic method or anaerobic methods in the absence of one another. The aerobic and anaerobic methods may be carried out separately or concurrently.

Provided herein is a system effective in bioaugmentation for treatment of PCB impacted sediments and other POP-contaminated environments. In one embodiment, the system does not interfere with the bioavailability of the POPs, such that it is effective to treat low levels of a POP in a contaminated environment. In a particular embodiment, the system is effective to treat low levels of weathered PCBs in sediment mesocosms. In another embodiment, the system includes substrata that do not inhibit the activity of the active inoculum. In a particular embodiment, the substratum is GAC, effective to enhance the overall bioaugmentation, as compared to administration without GAC. In another embodiment, the system includes an active inoculum that has sustained activity, such that the active inoculum has effective throughout the dechlorination process of PCBs and the active inoculum has a positive synergistic effect on the indigenous dehalorespiring population that contribute to the process.

In selection of a system of the invention, it will be appreciated that the compatibility of the active inoculum, the environment to be treated, the indigenous bacterial population of the environment and the substrata will all be considered.

In a further embodiment, the invention provides a method of making a system of the invention. Such method includes known methods for formation of a biofilm on an organic substratum, under conditions that permit formation of a biofilm on the substratum. A system of the invention may be made in advance of use or may be made at the time of use. In a particular embodiment, the system is made at the site of an environment to be treated.

In one embodiment, the active inoculum is applied to the substratum by spray application. Such application methods are particularly useful when the substratum is in a powdered or otherwise non-granular form. In another embodiment, the active inoculum is applied to the substratum by soaking and/or submersing the substratum into a cell culture containing the active inoculum.

Because many POP transforming bacteria are hydrophobic, organic substrata such as activated carbon can be used to effectively harvest and concentrate microorganisms from culture by surface adsorption without centrifugation or filtration. The organic substrata with adsorbed microbial catalysts as an active inoculum can then be used directly as inoculum in POP-contaminated sediments or soils.

Use of a system of the invention will enhance the microbial degradation of POPs, while simultaneously adsorbing hydrophobic POPs from the environment, making them bioavailable for the microorganisms located in the formed biofilms and, additionally, lowering the aqueous concentration of POPs that have detrimental effects towards fish and mammals as they bioaccumulate through the food chain.

Therefore, in one embodiment, the invention provides a method of inoculating microorganisms in an environment to degrade POPs in that environment by use of a system of the invention. When the system is used as a microbial inoculum delivery vehicle, the biofilm bacteria will enhance the degradation of POPs, while the contaminants present in the environment that are hydrophobic will adsorb to the organic surface of the substrata, thus increasing the bioavailable concentration of the POPs to the microorganisms and thereby enhancing the microbial degradation of POPs.

In a further embodiment, the invention provides a method of treating a POP-contaminated environment, e.g., aqueous environment containing sediment and/or soil, to reduce or remove POPs from the environment by use of a system of the invention.

The methods of the invention comprising inoculation and POP removal or reduction may be performed separately or concurrently.

The methods of the invention include introduction of an inert organic surface (substrata) where 1) the active inoculum of POP-degrading microorganisms are attached in biofilms and 2) the POP can adsorb onto. This two-phased approach provides an efficient and cost effective method for inoculation of microorganisms for bioaugmentation as well as keeping the POPs out of the water phase. Inert organic compounds such as activated carbon used for formation of the POP degrading biofilms are similar to naturally occurring organic compounds in the environment, making recovery of these compounds unnecessary by the end of the bioaugmentation period, since the biofilm coated compounds will blend in with the naturally occurring organic particles.

It was previously believed that a solid structure based POP removal system was not feasible in an in situ environment, largely because a number of factors, such as predation, competition and sorption, conspire against bioaugmentation in non-confined systems. The system and methods of the invention, however, overcome these issues, as organic substrata (such as activated carbon) have inherently high affinities for simultaneous attraction of POP degrading biofilm forming bacteria and adsorption of POPs, which ensures close proximity to bioavailable electron acceptors. As such, the structure of the system of the invention (i.e., the presence of both solid substrate and biofilm elements) enables implementation of a two-phased approach, where organic compounds are applied as substratum for biofilm formation and subsequent delivery vehicles for bioaugmentation of POPs in contaminated sediments and soils.

The advantages and features of the invention are further illustrated with reference to the following examples, which are not to be construed as in any way limiting the scope of the invention but rather as illustrative of embodiments of the invention in specific applications thereof.

Example 1

Organic Substrata as Microbial Inoculum Delivery Vehicles for Bioaugmentation of POP in Contaminated Sediments and Soils Absorbents such as granular activated carbon (GAC) have been used to sequester aromatic POPs in sediments to minimize their interaction with the biological food chain. However, it has been assumed that when sequestered from the biological food chain the POPs would no longer be bioavailable to microbial transformation. FIG. 1 shows that the rates of microbial reductive dechlorination of PCB in Baltimore harbor sediments were not significantly impacted by addition of GAC to contaminated sediments. Furthermore, the results also indicate that addition of GAC results in a more complete reductive dehalogenation of Aroclor 1260 based on higher occurrence of mono- and di-chlorinated homologs as precuts with GAC compared with a higher occurrence of tri-, tetra and penta-chlorinated homologs in cultures without GAC (FIG. 2). In FIG. 2 it is seen that dechlorination activity occurred in all microcosms independent of activated carbon, but that in the presence of activated carbon a higher proportion of PCBs were transformed into less chlorinated congeners that are accessible for aerobic degradation and subsequently complete mineralization.

Figure 3:
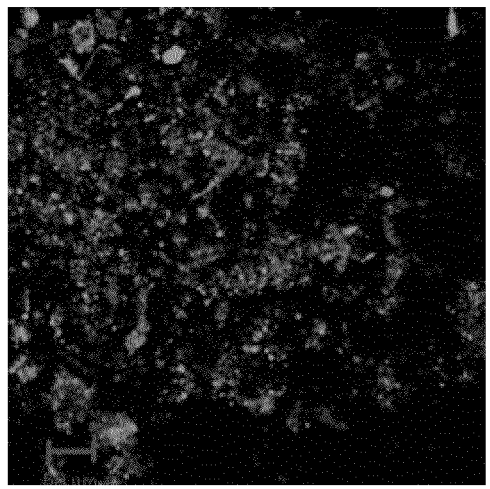
FIG. 3 is a micrograph from a Confocal Laser Scanning Microscope showing an example of a biofilm forming on a GAC particle. (10 times magnification.)

The results are consistent with GAC promotion of the microbial process, possibly by accumulating PCB to kinetically saturating concentrations in the immediate proximity of the microbial biofilms. An example of a microbial biofilm forming on a GAC particle is shown in FIG. 3, where biofilm bacteria were hybridized with the general probe for Bacteria EUB338 and attached to sediment particles mixed with activated carbon (10 times magnification).

Example 2

Simulation of In Situ Bioaugmentation of POP in Contaminated Sediments and Soils The effectiveness of using GAC for inoculating PCB dechlorinating microorganisms into PCB impacted sediments was successfully tested with *Dehalobium chlorocoercia*, DF-1. Sediments and water retrieved from a PCB contaminated site in the Baltimore Harbor were incubated with DF-1 using GAC as a carrier, where the incubation was at room temperature for 120 days.

*Dehalobium chlorocoercia* DF1 was grown anaerobically in estuarine mineral medium (EC1) as described previously (Berkaw, M., et al., Appl Environ Microbiol. 1996, 62, 2534-

2539; Wu, Q., et al. *Environ. Sci. & Technol.,* 2002, 36, 3290-3294.) Sodium formate was added as the electron donor at a final concentration of 10 mM and PCB 61 (2,3,4,5-PCB) was added in acetone (0.1% v/v) at a final concentration of 173 µM. *Desulfovibrio* sp. extract was added as a growth factor at a final concentration of 1% (v/v). Titanium(III) nitrilotriacetate (0.5 mM, TiNTA) was used as a chemical reductant to remove oxygen from the medium. *D. chlorocoercia* DF-1 was routinely grown in 50 ml of medium in 160-ml serum bottles sealed with 20-mm Teflon-coated butyl stoppers (West Co., Lionville, Pa.). All cultures were incubated statically at 30° C. in the dark. Growth was monitored by gas chromatographic analysis of PCB 61 dechlorination to PCB 23 (2,3,5-PCB) and by quantitative PCR of 16S rRNA gene copies (described below).

Mesocosm Experiments

Mesocosms were prepared in glass 2 liter TLC tanks (Fisher Scientific). PCB impacted sediments were sampled on 14 May 2009 from the Northwest Branch of Baltimore Harbor (BH) with a petite Ponar grab sampler at 39°16.8_N, 76°36.2_W and stored in the dark under nitrogen for 19 days at 4° C. prior to use. Sediment was homogenized anaerobically by stirring in an anaerobic glove bag and 1 liter of the homogenized sediment was added to each mesocosm tank with 2 cm of indigenous water above the sediment surface. A glass plate covered each mesocosm to minimize evaporation with a 1 cm gap on one end for air exchange. Water lost due to evaporation was periodically replenished with deionized water to maintain the original salts composition and osmolarity of the harbor water.

The bioaugmentation inoculum was prepared using ten 50 ml cultures of DF1 grown until approximately 50% of PCB 61 was dechlorinated to PCB 23. The cultures were transferred into 250 ml Oak Ridge bottles in an anaerobic glove box and sealed under a nitrogen-carbon dioxide (4:1) atmosphere. The bottles were centrifuged at 22,000×g for 30 min, decanted, and the pellets were pooled by resuspension in 50 ml of sterile ECl medium. The concentration of pooled DF1 was approximately $5 \times 10^7$ 16S rRNA gene copies per ml. Spent medium supernatant was prepared by passing culture supernatant through a 0.22 micron filter (Millipore, www.millipore.com) to remove residual DF1 cells. Mesocosms were amended with one of 4 treatments in an anaerobic glove box:

(1) 20 ml of concentrated DF1 (about $5 \times 10^7$ cells per ml);
(2) 20 ml of spent growth media;
(3) 20 ml of concentrated DF1 adsorbed to 25 g granulated activated carbon for 1 hour; or
(4) 20 ml of spent growth media adsorbed to 25 g activated carbon for 1 hour.

No exogenous electron donor was added. Mesocosms were homogenized by stirring with a Teflon spoon, then removed from the anaerobic glove box and incubated at 23° C. in the dark. Mesocosms were periodically sampled by taking 6 cm deep cores using a 5 ml syringe barrel with the end cut off. Triplicate cores (5 ml) were sampled for each timepoint using a random sampling grid and homogenized prior to analysis for PCBs and DNA as described below.

DNA Extraction

DNA was extracted by adding 0.25 g of sediment from each sample core to a PowerBead microfuge tube of a Power Soil DNA Isolation Kit (MOBIO Laboratories, Inc. www.mobio.com). The PowerBead tubes were mixed by hand prior to 30 s of bead beating at speed "4.5" using a FastPrep120 (Q-Biogene, 8 CA). Total DNA was then isolated from the PowerBead tubes according to the manufacturer's directions. DNA was eluted in 100 µl of TE buffer and quantified with a NanoDrop 1000 Spectrophotometer (ThermoScientific). All DNA samples were diluted to 2 ng/ul in TE buffer prior to analysis by qPCR or DHPLC.

Enumeration of PCB Dehalorespiring Bacteria by Quantitative PCR

The quantification of Chloroflexi 16S gene copies in each subcore was performed by quantitative PCR using iQ SYBR green supermix (Bio-Rad Laboratories, Hercules, Calif.) and gene-specific primers for the 16S rRNA gene of the dechlorinating Chloroflexi (348F/884R) (Fagervold, S. K., et al. *Appl. Environ. Microbiol.* 2005, 71, 8085-8090.). Each sample mixture had a 25-µl reaction volume containing 1× iQ SYBR green supermix, forward and reverse primers at a concentration of 500 nM, and 1 µl of the prepared DNA. PCR amplification and detection were conducted in an iCycler (Bio-Rad Laboratories, Hercules, Calif.). Quantitative PCR conditions were as follows: initial denaturation for 15 min at 95° C. followed by 35 cycles of 30 s at 95° C., then 30 s at 61° C., then 30 s at 72° C. One copy of the gene per genome was assumed based on the genomes of *Dehalococcoides ethenogenes* strain 195 and *Dehalococcoides* sp, strain CBDB1 (Seshadri, R., et al., *Science.* 2005, 307, 105-108; Kube, M. et al., *Nat. Biotech.,* 2005, 23, 1269-73). QPCR data was analyzed with the MJ Opticon Monitor Analysis Software v3.1 and compared to a standard curve of bona fide DF1 348F/884R 16S rRNA gene product. Amplification efficiencies were 80% or greater.

Community Analysis of PCB Dechlorinating Bacteria by Denaturing HPLC

Denaturing HPLC (DHPLC) analyses were performed using a WAVE 3500 HT system (Transgenomic, Omaha, Nebr.) as described previously (Kjellerup, B. V., et al., *Environ Microbiol.,* 2008, 10, 1296-1309) except that the instrument was equipped with a florescence detector (excitation 490 nm, emission 520 nm). The primer set 348F/884R was used for specific PCR amplification of 16S rRNA genes from dechlorinating bacteria within the Chloroflexi (Fagervold, S. K., et al. *Appl. Environ. Microbiol.* 2005, 71, 8085-8090.). DNA was amplified by PCR in 50 µl reaction volumes as described previously and PCR products of the correct length were confirmed by electrophoresis using a 1.5% agarose gel. The 16S rRNA gene fragments were analyzed in a 10 µl injection volume by DHPLC with a DNASep® cartridge packed with alkylated nonporous polystyrene-divinylbenzene copolymer microspheres for high-performance nucleic acid separation (Transgenomic, Omaha, Nebr.). The oven temperature was 63.0° C. and the flow rate was 0.5 ml min$^{-1}$ with a gradient of 55%-35% Buffer A and 45%-65% Buffer B from 0-13 minutes. Analysis was performed using the Wavemaker version 4.1.44 software. Individual peaks were eluted for sequencing and collected with a fraction collector based on their retention times. Prior to sequencing individual fractions were dried, dissolved in 15 µl nuclease free water and re-amplified following the protocol described above. PCR products were confirmed by DHPLC to ensure that only one species was present, then purified subsequently by electrophoresis in a 1.5% low melt agarose gel purification of excised fragments using Wizard® PCR Preps DNA Purification Resin/A7170 (Promega Corp., Madison, Wis.).

DNA Sequencing and Analysis

DHPLC fractions were sequenced in the 5' and 3' direction with 250 pM of primer 348F or 884R and 5% DMSO to reduce effects from potential secondary structure using the BigDye® Terminator v3.1 (Applied Biosystems, Foster City, Calif.) kit following manufacturer's instructions. Sequencing of purified DNA was performed on an ABI 3130 XL automated capillary DNA sequencer (Applied Biosystems, CA).

At least 468 nts of sequence from each phylotype were obtained in this manner. Sequence similarities were analyzed using the Basic Local Alignment Search Tool (BLAST). A phylogenetic tree was drawn using the Tree Builder software found at the Ribosomal Database Project (http://rdp.cme.msu.edu/index.jsp).

PCB Extraction

Sediment samples were extracted using an Accelerated Solvent Extractor (Dionex) following EPA method 3545. Approximately 5 grams wet weight sediment was dried with pelletized diatomaceous earth at room temperature in a desiccator containing $CaCl_2 \cdot 2H_2O$. The dried sediment (approximately 1 g) was transferred to an 11 ml stainless steel extraction cell containing 0.6 g Cu and 2.4 g fluorosil between two cellulose filters on the bottom of the cell and the remaining cell volume was filled with anhydrous $Na_2SO_4$. To correct for extraction efficiency, 10 µl of a 400 µg $l^{-1}$ solution of PCB 166 in hexane was pipetted on top of the $Na_2SO_4$. The sample containing the surrogate was extracted with approximately 20 ml of hexane at 100° C. and purged with 1 MPa nitrogen. The sample was evaporated to a final volume of 1 ml at 30° C. under nitrogen using a N-EVAP 111 nitrogen evaporator (Organomation Associates, Inc. Berlin Mass., US). Before PCB analysis, 10 µl of PCB 30 and PCB 204 (400 µg $l^{-1}$ each in acetone) was added to the sample as internal standards.

PCB Analysis

PCB congeners were analyzed using a Hewlett-Packard 6890 series II gas chromatograph (GC) with a DB-1 capillary column (60 m by 0.25 mm by 0.25 µm; JW Scientific, Folsom, Calif.) and a $^{63}Ni$ electron capture detector by a modified method of EPA 8082. PCB congeners in a mixture containing 250 µg $l^{-1}$ Aroclor 1232, 180 µg $l^{-1}$ Aroclor 1248 and 180 µg $l^{-1}$ Aroclor 1262 were quantified with a 10-point calibration curve using PCB 30 and PCB 204 as internal standards. Individual congeners and respective concentrations were obtained from Mullin et al. (Environ. Sci. Technol., Vol. 18, No. 6, 468-476 (1984)). Fifty-five additional congeners not present in the Aroclor mixture that were potential dechlorination products were added to the calibration table containing the Aroclor congeners. The additional congeners were quantified with 10-point calibration curves at concentrations of 2, 5, 10, 20, and 40 µg $l^{-1}$ (in duplicate) for the low range calibration and 40, 100, 200, 400, and 800 µg $l^{-1}$ (in duplicate) for the high range calibration. Using this protocol 173 congeners were resolved in 130 individual peaks (not including the standards PCB 30 and PCB 204 and the surrogate PCB 166). Co-eluting peaks were indicated as multiple congeners. The final concentration of individual congeners in samples was corrected for the recovery efficiency of the surrogate (typical recovery efficiencies were 75% or greater).

Effects of Treatments on Reductive Dechlorination of Weathered PCBs

BH sediment mesocosms were bioaugmented with dehalorespiring *D. chlorocoercia* DF-1 to a final concentration of approximately $5 \times 10^5$ cells $ml^{-1}$ and the PCB congeners were monitored over 120 days. In mesocosms bioaugmented directly and with GAC as a solid substrate, there was a net decrease in the total amounts of penta- through octa-PCBs and a net increase in the total amount of tetra- and tri-PCBs over the course of 120 days (FIG. 5). There was no obvious change in homolog distribution in non-bioaugmented mesocoms treated with spent medium or spent medium and GAC. Bioaugmentation both directly and with GAC as a carrier substrate resulted in 0.6 to 0.7 mol Cl per biphenyl dechlorinated, respectively, after 120 days (FIG. 6). Bioaugmentation with GAC had a slightly greater rate of dechlorination (0.0067 Cl/biphenyl/day) compared with direct injection (0.0041 Cl/biphenyl/day). A t-Test (two-sample assuming unequal variances, $\alpha=0.05$) showed a significant difference in dechlorination rates between the bioaugmentation treatments with a P-value of 0.041 (df=4).

Single congener analysis of mesocosms bioaugmented with DF1 resulted in a significant decrease in higher chlorinated congeners and corresponding increase in less chlorinated congeners (FIG. 4). The total mol sum of predicted substrates and products was $1.26 \pm 0.307 \times 10^{-9}$ mol per gram sediment at day 0 and $1.02 \pm 0.639 \times 10^{-9}$ mol per gram sediment at day 120. The amount of substrate congeners decreased from $1.00 \pm 0.228$ to $0.291 \pm 0.282 \times 10^{-9}$ mol per gram sediment and the amount of product congeners increased from $0.256 \pm 0.0786$ to $0.729 \pm 0.356 \times 10^{-9}$ mol per gram sediment. The difference in mol PCB might have resulted from the absence of possible dechlorination products in the GC method or aerobic degradation by indigenous microorganisms. Strikingly, PCB 194 decreased from about 23 to 8 ppb, and PCB 133, the predicted product of the double flanked reductive dechlorination of PCB 194 was found to increase from about 1 to 12 ppb over 120 days. Terminal products of double flanked reductive dechlorination of PCB 180 (PCB153) and PCB 174 (PCB135) were detected after 120 days, however, these products did not accumulate to substantial amounts. Furthermore, predicted products of doubly flanked reductive dechlorination of the remaining octa- and hepta-chlorinated congeners were not detected and the less chlorinated congeners that did accumulate were not products resulting from dechlorination of double flanked chlorines. Since DF-1 can only reductively dechlorinate doubly flanked chlorines the dechlorination products result from enhanced activity by the indigenous population of dehalorespiring bacteria. Addition of cell free medium used to grow DF-1 did not stimulate PCB dechlorination, indicating that the enhanced activity by indigenous microorganisms was the direct result of bioaugmentation with DF-1 cells and did not result from "priming" by residual PCBs or biostimulation by the medium.

Example 3

Sustainability of *D. Chlorocoercia* DF1 after Bioaugmentation

Figure 7:
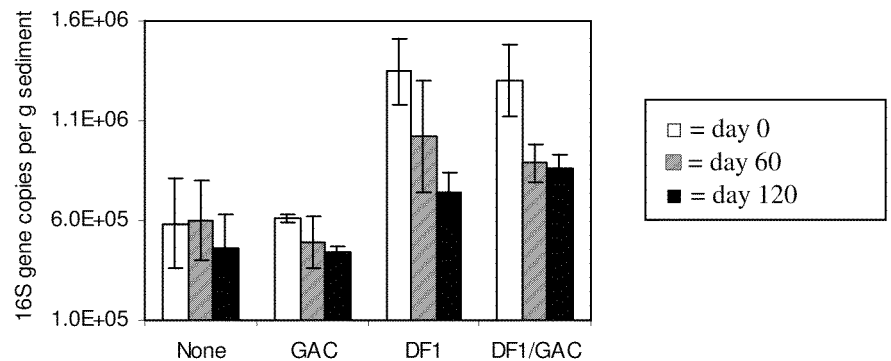
FIG. 7 is a graph with the enumeration of total dechlorinating Chloroflexi normalized to 16S rRNA gene copies/gram sediment at day 0, 60 and 120.

To determine whether DF-1 was sustainable in the presence of relatively low PCB concentrations and the indigenous general microbial community of dehalorespiring and non-dehalorespiring bacteria within the sediment, dehalorespiring microorganisms were enumerated during growth based on the number of 16S rRNA gene copies per gram dry sediment. In both bioaugmented mesocosms the numbers of dehalorespiring bacteria was initially about 2-fold higher then in untreated mesocosms ($1.3 \times 10^6$ compared to about $6.0 \times 10^5$ copies per gram, respectively) indicating that DF-1 accounted for approximately half the total population of dehalorespiring bacteria. A Student's t-Test (two-sample assuming unequal variances, $\alpha=0.05$) showed a significant difference between initial 16S rRNA gene copy numbers between treatments with a two-tail P-value of 0.01 (df=3). The total 16S rRNA copy numbers in treated mesocosms decreased by 60 days before reaching an apparent steady state for the 120 day incubation period (FIG. 7). However, for bioaugmentation treatments by both direct injection and on GAC substrate, the total number of dehalorespiring microorganisms remained nearly 2-fold higher in the bioaugmented mesocosms compared with the untreated mesocosms (about $8.0 \times 10^5$ compared to about $4.5 \times 10^5$ copies per gram at day 120, respectively). The results indicate that total number of dehalorespiring microorganisms in the mesocosms bioaugmented with DF1 were maintained at higher numbers during active dechlorination of the weathered Aroclor compared with non-bioaugmented controls.

Figure 8:
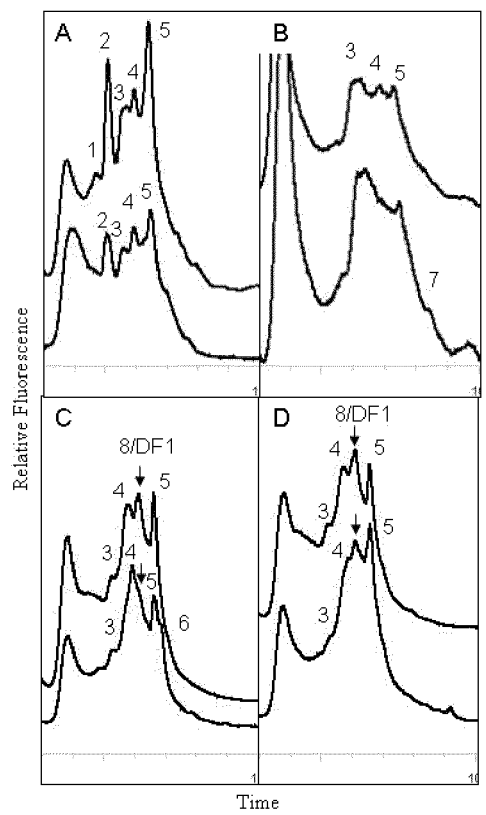
FIG. 8 is a DHPLC community analysis of dechlorinating Chloroflexi 16S rRNA genes in mesocosms at day 0 (bottom trace) and day 120 (top trace): (A) spent growth media, (B) spent growth media+GAC, (C) DF1, and (D) DF1+GAC.

Seven predominant dehalorespiring phylotypes were detected by DHPLC in the BH sediment mesocosms. The community was generally similar between mesocosms, with the exception of DF1, which was only detected in bioaugmented mesocosms, and did not change greatly over 120 days (FIG. 8). The putative DF1 fraction was collected, sequenced, and found to be 100% identical to DF1. One phylotype present at time zero (BH 4) was 100% identical to phylotype DEH10, previously detected BH sediment microcosms (Fagervold, S. K., et al. *Appl. Env. Microbiol.* 2007, 73, 3009-18; Fagervold, S. K., et al. *Appl. Env. Microbiol.* 2005, 71, 8085-90.), but no other previously reported BH phylotypes were detected. Aside from the phylotype indentified as DEH10, the other dehalorespiring Chloroflexi did not group in the *Dehalococcoides* clade.

Example 4

Simulation of In Situ Bioaugmentation of POP in Contaminated Sediments and Soils Sediments retrieved from a PCB contaminated site in the Baltimore Harbor were simultaneously bioaugmented with aerobic PCB degrader *Burkholderia xenovorans* LB400 and anaerobic PCB dechlorinator DF1 inoculated as biofilm on GAC. Lactate was added as electron donor.

Individual mesocosms were prepared with 1 liter of sediment and 5-8 ppm of weathered Aroclor 1260 and were inoculated with one of the following:
 spent growth medium and 1% GAC;
 lactate and 1% GAC;
 LB400 and 1% GAC and lactate; and
 LB400 and DF-1 and 1% GAC and lactate.

Figure 10:
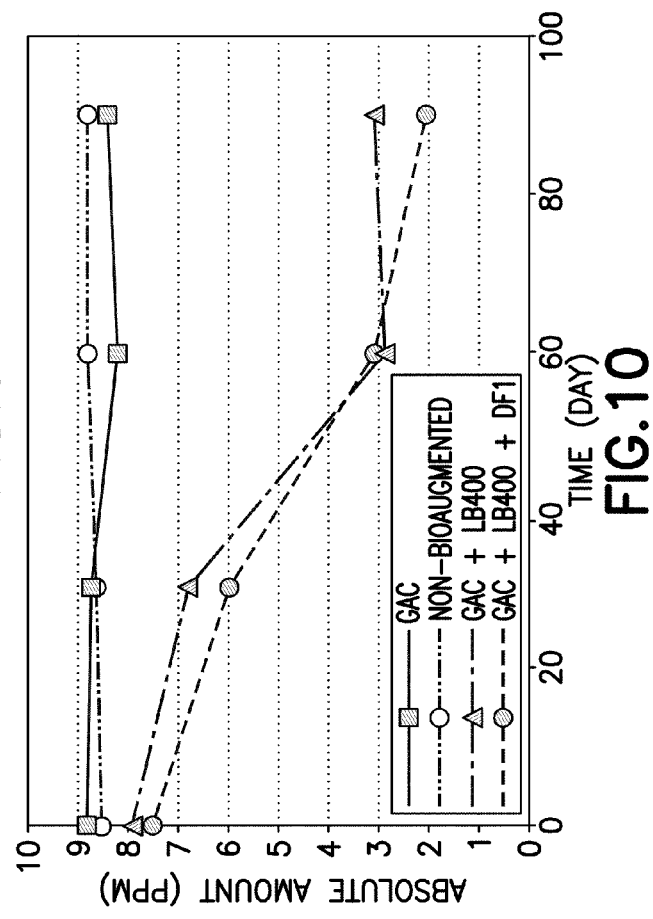
FIG. 10 is a graph demonstrating the changes in absolute amount of PCBs in mesocosms containing sediment contaminated with low levels of Aroclor 1260 over time after treatment with an anaerobic PCB dechlorinator and an aerobic degrader, as described in Example 4.
Figure 11:
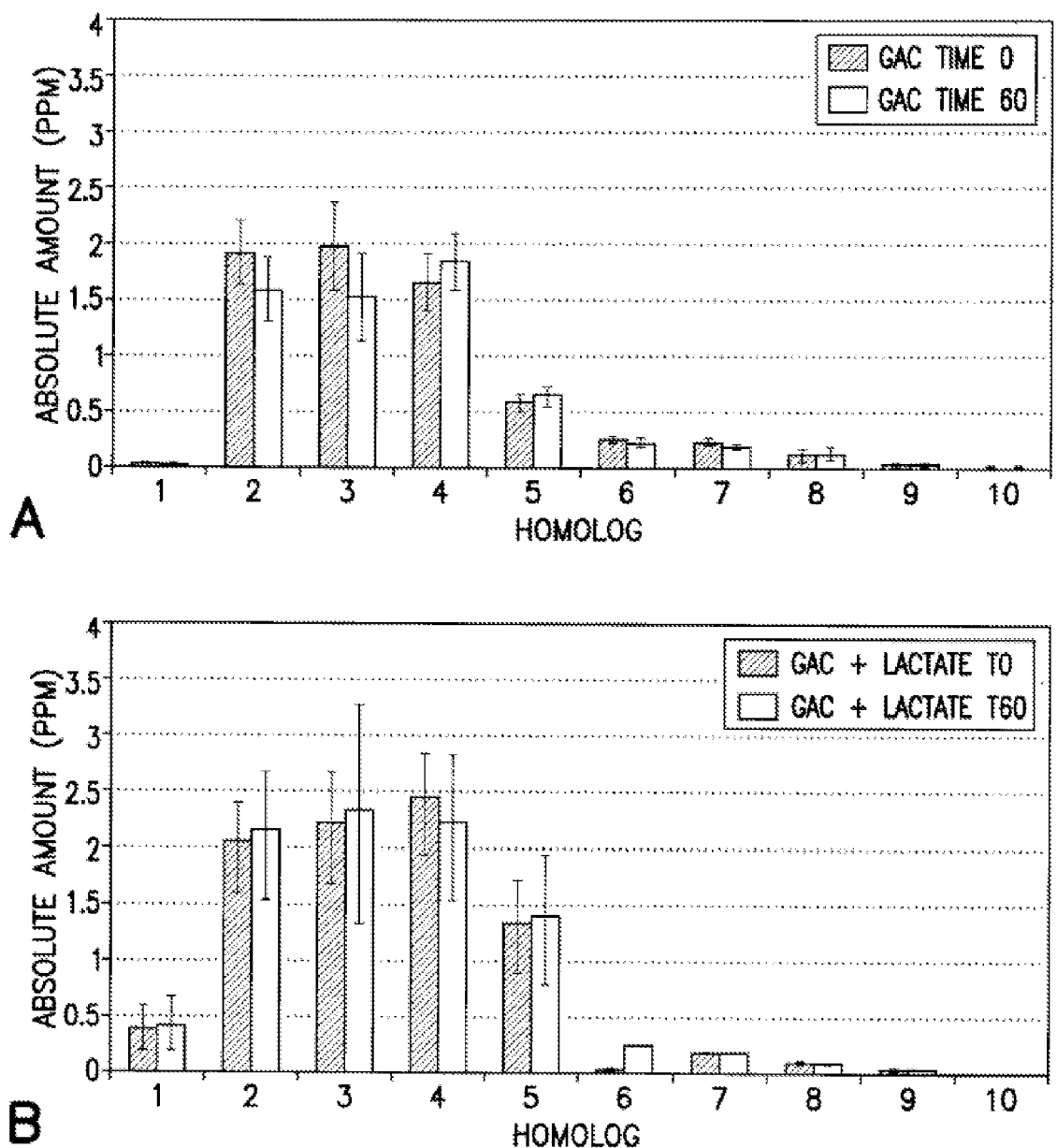
FIG. 11 is a graph demonstrating PCB analysis by homolog at day 0 (gray bars) and day 120 (black bars) after treatment as described in Example 4, with (A) spent growth medium and GAC, (B) GAC and lactate, (C) GAC, lactate and LB400, and (D) GAC, lactate, LB400 and DF-1.
Figure 11:
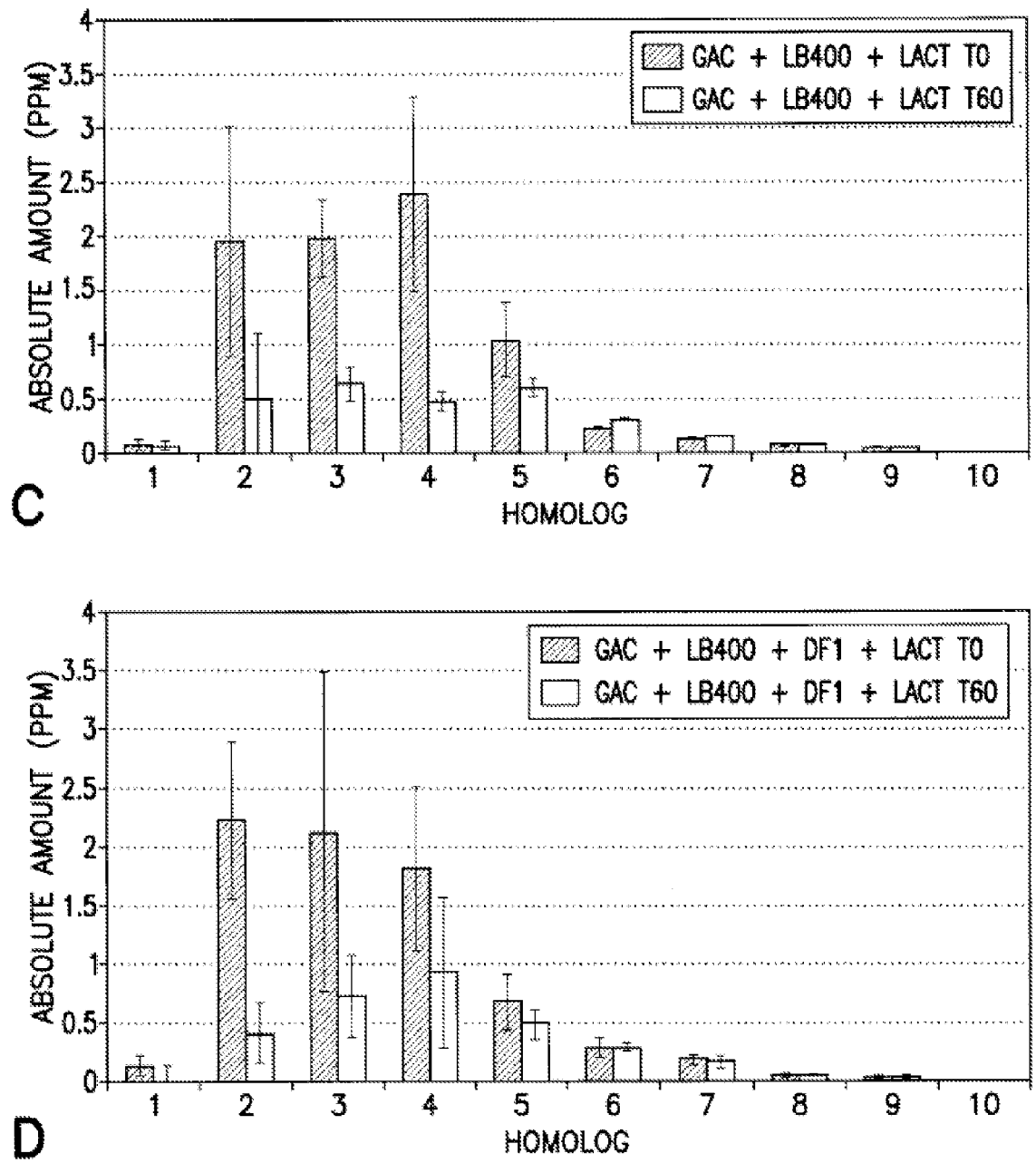
Figure 12:
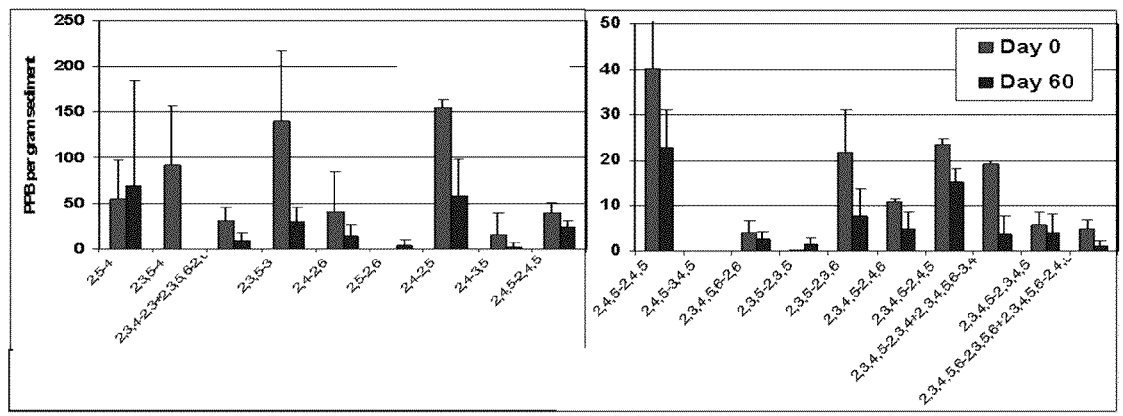
FIG. 12 is a graph demonstrating the effect of GAC, DF-1 and LB400 on PCB congeners.
Figure 13:
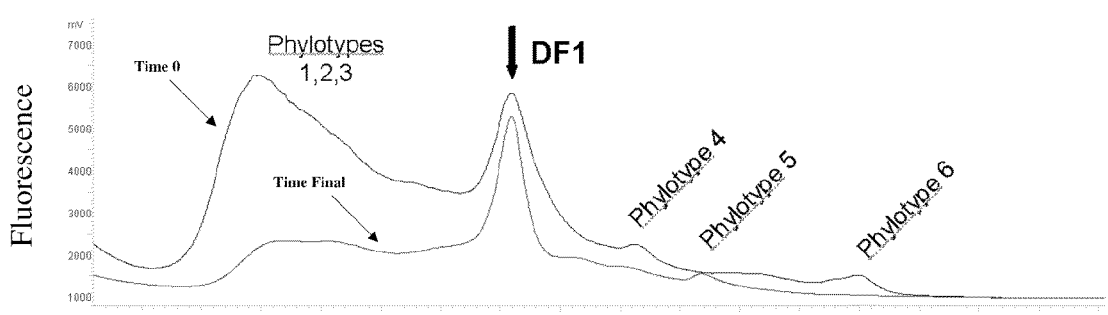
FIG. 13 is a graph illustrating DHPLC community analysis of dechlorinator phylotypes in a mesocosm with DF-1 and LB400.
Figure 14:
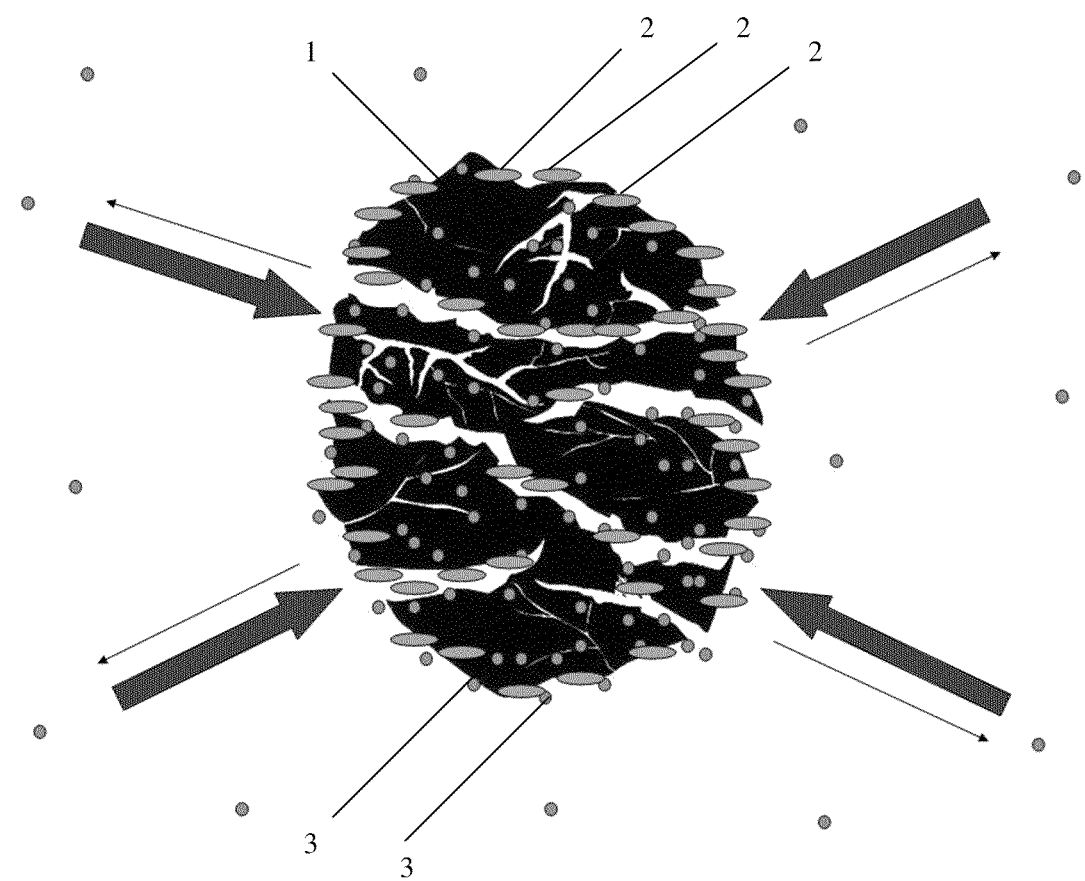
FIG. 14 is an illustrative model of a system of the invention, with a substratum 1, active inoculum 2 adsorbed as a biofilm and adsorbed POPs 3.

Results in FIG. 10 provide data for days 0 to 90 after inoculation, which demonstrate significant dechlorination and degradation of PCB after bioaugmentation with both the anaerobe and aerobe together using GAC. It is seen that there was a net decrease of mono- through nona-PCBs and that 75% of the PCBs were degraded in 90 days. Addition of GAC did not have an adverse effect on the dechlorination and/or degradation. FIG. 11 provides the data for PCB analysis by homolog at day 0 (gray bars) and day 60 (black bars) after treatment with (A) spent growth medium and GAC, (B) GAC and lactate, (C) GAC, lactate and LB400, and (D) GAC, lactate, LB400 and DF-1. FIG. 12 illustrates that the addition of DF-1 and LB400 together resulted in the degradation of higher and lower chlorinated PCBs without net accumulation of less chlorinated PCB dechlorination products. FIG. 13 shows the presence of DF-1 at both days 0 and 90. It is contemplated that incubation for 120 days will result in continued dechlorination and degradation of the PCBs.

While the invention has been has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A system for at least partially degrading persistent organic pollutants (POPs) in soil or sediment, the system comprising:
 an inert substratum effective to adsorb hydrophobic POPs from the soil or sediment, said inert substratum comprising granular activated carbon; and
 a biofilm on the substratum, wherein the biofilm comprises an active inoculum; wherein POPs comprise polychlorinated biphenyls (PCBs), and wherein the active inoculum comprises dehalorespiring bacteria or PCB oxidizing bacteria capable of selectively degrading PCBs.

2. A method of making a system for at least partially degrading persistent organic pollutants (POPs) in soil or sediment, comprising:
 harvesting POP-degrading or POP transforming microorganisms from a culture thereof to form an active inoculum;
 providing a substratum effective to adsorb hydrophobic POPs from the soil or sediment, said substratum comprising granular activated carbon; and
 applying the active inoculum to the substratum wherein POPs comprise PCBs, and wherein the active inoculum comprises dehalorespiring bacteria or PCB oxidizing bacteria capable of selectively degrading PCBs to form a biofilm on said substratum.

3. A method of treating a persistent organic pollutant (POP)-containing environment comprising soil or sediment, the method comprising administration of a system to the POP-containing environment, the system comprising:
 an inert substratum effective to adsorb hydrophobic POPs from the soil or sediment, said substratum comprising granular activated carbon; and
 a biofilm on the substratum, wherein the biofilm comprises an active inoculum, the active inoculum comprises dehalorespiring bacteria or PCB oxidizing bacteria, wherein POPs comprise PCBs, and wherein the system is effective to at least partially reduce the concentration of PCBs in the environment.

4. The method of claim 3, wherein the soil or sediment is in situ.

5. The method of claim 3, wherein the soil or sediment is in a closed or confined system.

6. The method of claim 5, wherein the closed or confined system is an aquaculture system.

7. A method of degrading persistent organic pollutants (POPs), in a locus containing the same, the method comprising introducing to said locus a biofilm comprising an active inoculum supported on a substratum comprising granular activated carbon, wherein the locus comprises soil or sediment, wherein POPs comprise PCBs, and the active inoculum comprises dehalorespiring bacteria or PCB oxidizing bacteria, and wherein the system is effective to degrade the POPs and/or making them more subject to degradation.

8. A method of bioaugmenting an aerobic degradation system, the method comprising administering to the aerobic degradation system an anaerobic dechlorination system in an environment comprising soil or sediment containing POPs, the anaerobic dechlorination system comprising:
 an inert substratum effective to adsorb hydrophobic POPs from soil or sediment; and
 a biofilm on the substratum, wherein the biofilm comprises an active inoculum, wherein POPs comprise PCBs, and the active inoculum comprises dehalorespiring bacteria or PCB oxidizing bacteria capable of selectively degrading PCBs.

9. The method of claim 8, wherein the administration of the anaerobic dechlorination system is performed concurrently with degradation by the aerobic degradation system.

10. The system of claim 1, wherein the bacteria is dehalorespiring bacteria selected from the group consisting of *Dehalococcoides* spp., *Dehalobium* spp., *Desulfitobacterium* spp., *Desulfomonile* spp., and *Geobacter* spp.

11. The method of claim 2, wherein the bacteria is dehalorespiring bacteria selected from the group consisting of *Dehalococcoides* spp., *Dehalobium* spp., *Desulfitobacterium* spp., *Desulfomonile* spp., and *Geobacter* spp.

12. The method of claim 3, wherein the bacteria is dehalorespiring bacteria selected from the group consisting of *Dehalococcoides* spp., *Dehalobium* spp., *Desulfitobacterium* spp., *Desulfomonile* spp., and *Geobacter* spp.

13. The method of claim 7, wherein the bacteria is dehalorespiring bacteria selected from the group consisting of *Dehalococcoides* spp., *Dehalobium* spp., *Desulfitobacterium* spp., *Desulfomonile* spp., and *Geobacter* spp.

14. The method of claim 7, wherein the biofilm comprising an active inoculum supported on a substratum comprising granular activated carbon is effective to selectively degrade the POPs.

\* \* \* \* \*

UNITED STATES PATENT AND TRADEMARK OFFICE
CERTIFICATE OF CORRECTION

| | | |
|---|---|---|
| PATENT NO. | : 8,945,906 B2 | Page 1 of 1 |
| APPLICATION NO. | : 13/177436 | |
| DATED | : February 3, 2015 | |
| INVENTOR(S) | : Kevin R. Sowers | |

It is certified that error appears in the above-identified patent and that said Letters Patent is hereby corrected as shown below:

Title Page, Item 56, OTHER PUBLICATIONS: "Kobe, M., et al." should be -- Kube, M., et al. --.

Title Page, Item 74: "Hultguist, PLLC" should be -- Hultquist, PLLC --.

Signed and Sealed this
Fifth Day of May, 2015

Michelle K. Lee
*Director of the United States Patent and Trademark Office*